United States Patent
Morimoto et al.

(10) Patent No.: US 12,185,911 B2
(45) Date of Patent: Jan. 7, 2025

(54) TREATMENT TOOL ELEVATING MECHANISM AND ULTRASONIC ENDOSCOPE

(71) Applicant: FUJIFILM Corporation, Tokyo (JP)

(72) Inventors: Yasuhiko Morimoto, Kanagawa (JP); Tsuneo Fukuzawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 413 days.

(21) Appl. No.: 17/747,995

(22) Filed: May 18, 2022

(65) Prior Publication Data
US 2022/0400934 A1  Dec. 22, 2022

(30) Foreign Application Priority Data
Jun. 16, 2021  (JP) ................. 2021-100120

(51) Int. Cl.
| | | |
|---|---|---|
| *A61B 1/00* | (2006.01) | |
| *A61B 1/018* | (2006.01) | |
| *A61B 1/06* | (2006.01) | |
| *A61B 8/12* | (2006.01) | |

(52) U.S. Cl.
CPC .......... *A61B 1/00098* (2013.01); *A61B 1/018* (2013.01); *A61B 1/0623* (2013.01); *A61B 8/12* (2013.01)

(58) Field of Classification Search
CPC ..... A61B 1/00098; A61B 1/18; A61B 1/0623; A61B 1/00071; A61B 1/0055; A61B 1/051; A61B 1/126; A61B 8/12; A61B 8/5215
USPC ........................................ 600/107
See application file for complete search history.

(56) References Cited

U.S. PATENT DOCUMENTS 7,771,349 B2  8/2010  Kohno
2016/0270636 A1*  9/2016  Iwasaka ............. A61B 1/00137

FOREIGN PATENT DOCUMENTS

JP  2005287593  10/2005

* cited by examiner

*Primary Examiner* — Timothy J Neal
*Assistant Examiner* — James Edward Boice
(74) *Attorney, Agent, or Firm* — JCIPRNET

(57) ABSTRACT

Provided are a treatment tool elevating mechanism and an ultrasonic endoscope capable of restraining an increase in diameter of an endoscope and bearing a load.

The treatment tool elevating mechanism includes: a rotary shaft portion that is supported so as to be rotatable about a rotation axis; an elevator that is connected to one end of the rotary shaft portion so as to be rotatable integrally with the rotary shaft portion; and an elevating lever that is connected to the other end of the rotary shaft portion so as to be rotatable integrally with the rotary shaft portion, in which a rotational force is applied to the elevating lever, and the rotational force is transmitted to the elevator through the rotary shaft portion, at least one fitted member of the elevating lever or the elevator has a fitting recessed portion that is open in a direction of the rotary shaft portion, the rotary shaft portion has a fitting protruding portion that is fitted into the fitting recessed portion so as to be non-rotatable relative to the fitting recessed portion, and the fitting protruding portion has a center of gravity at a position eccentric from the rotation axis in a cross-section perpendicular to the rotation axis.

12 Claims, 10 Drawing Sheets

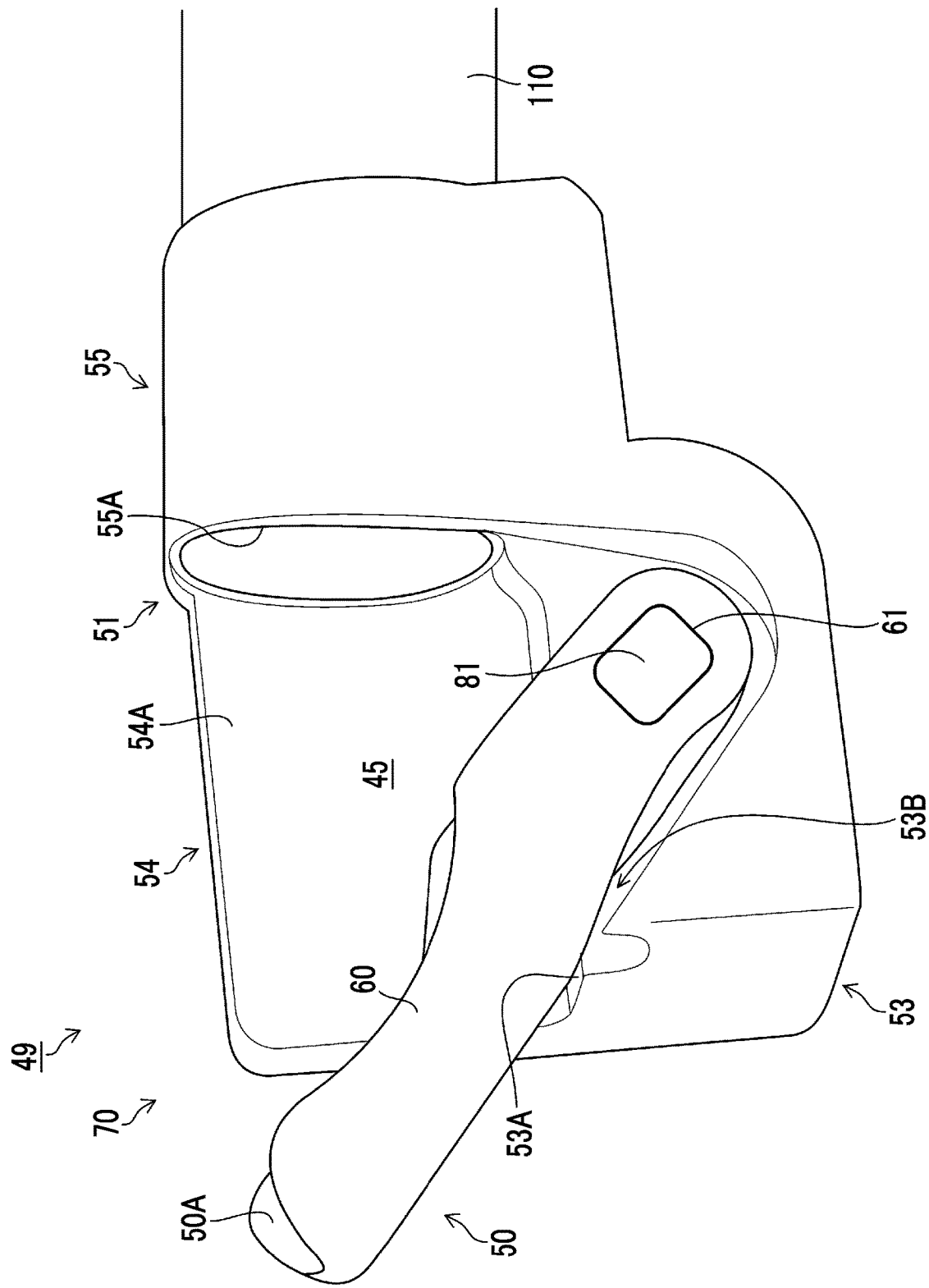

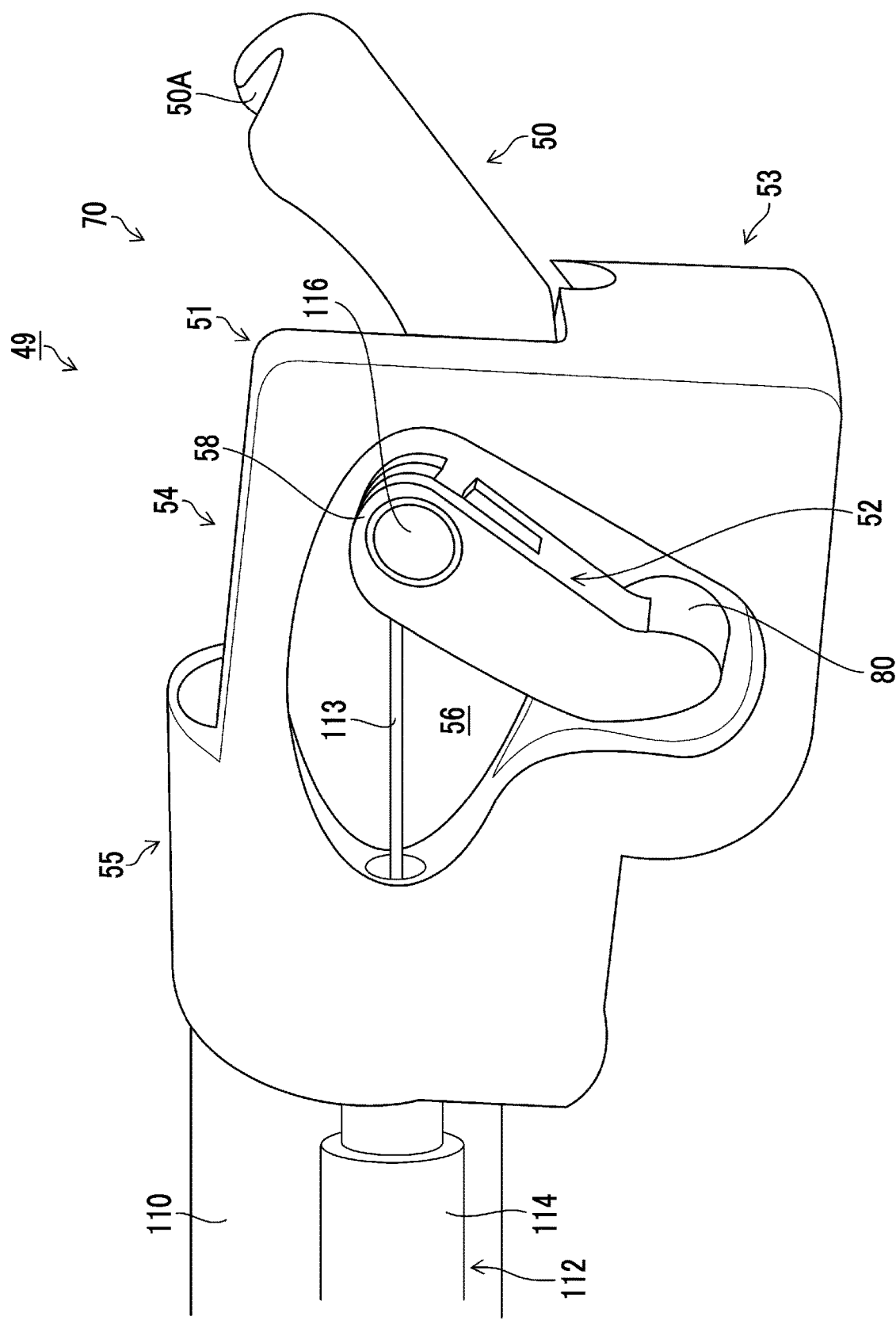

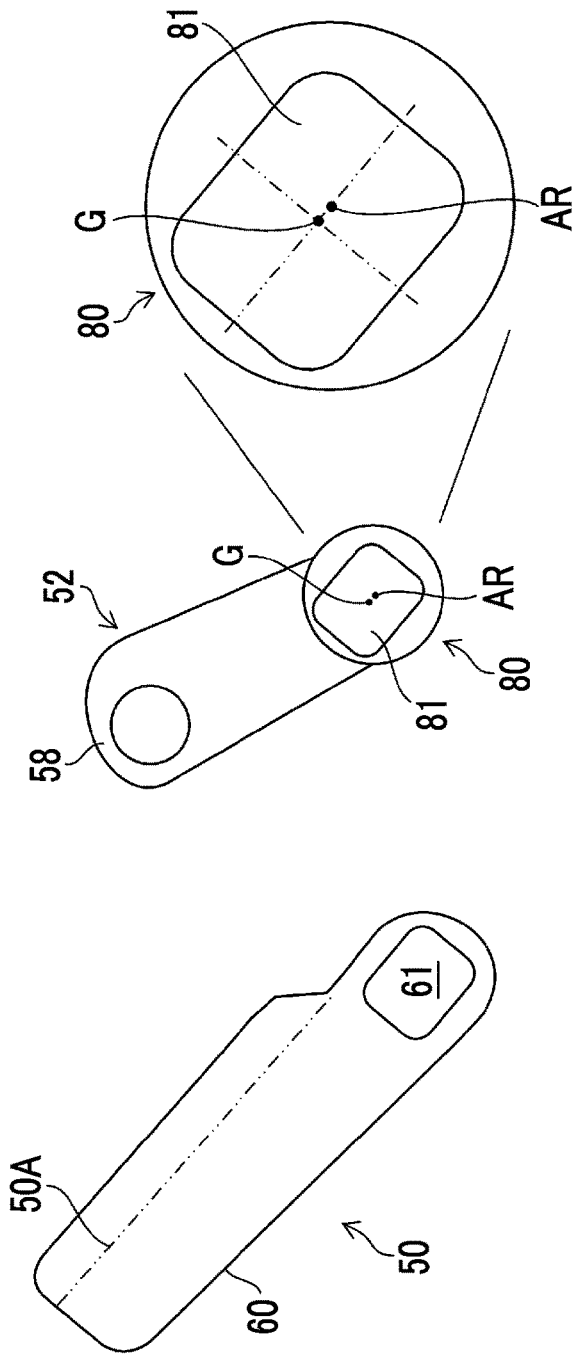
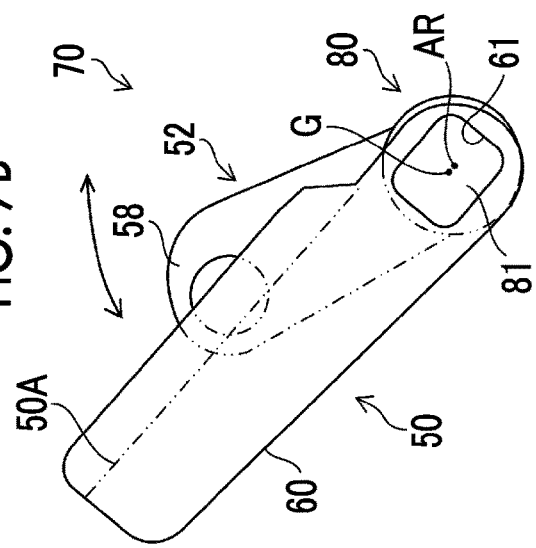

FIG. 8
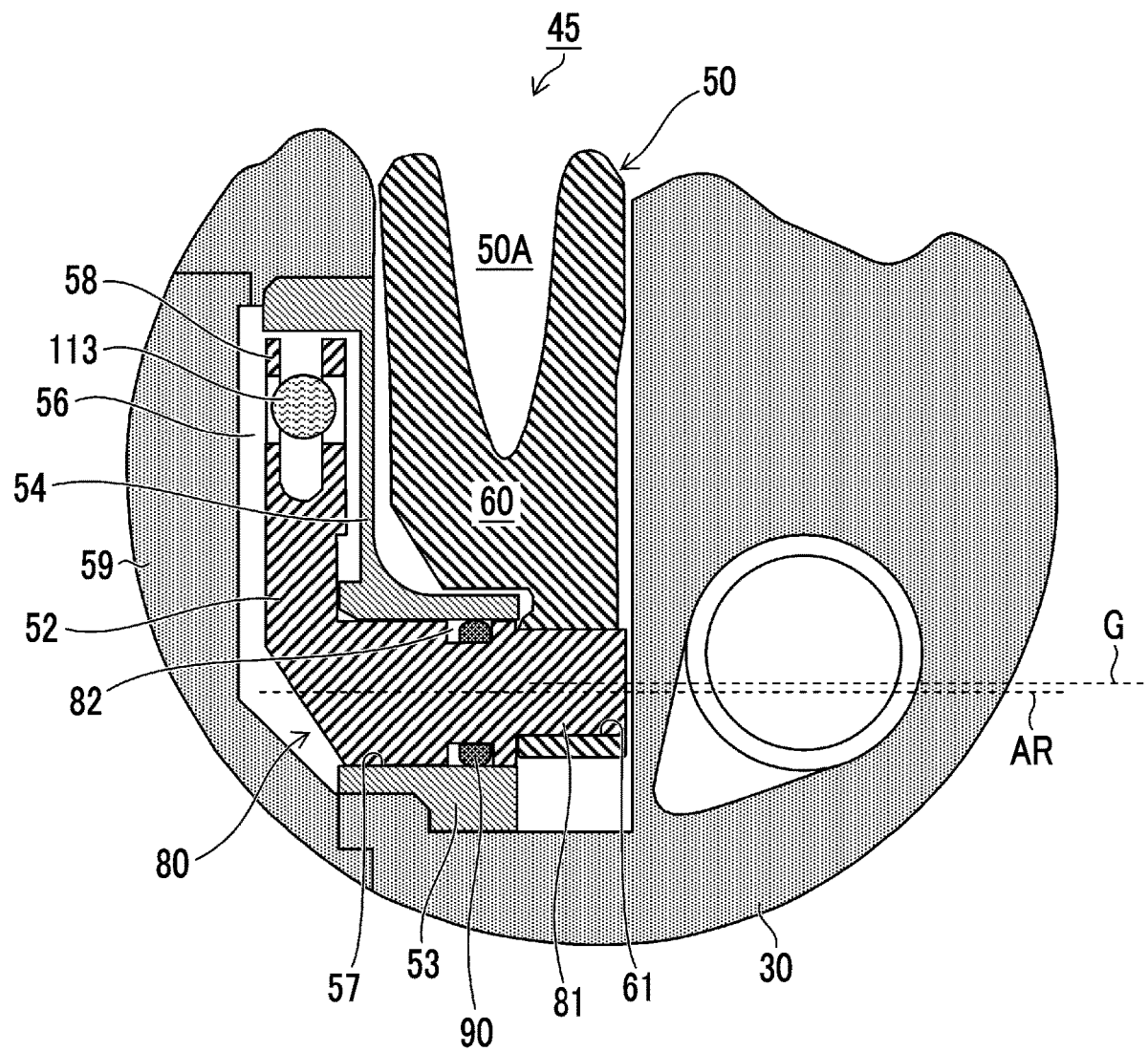
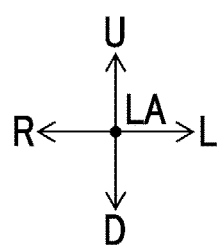

TREATMENT TOOL ELEVATING MECHANISM AND ULTRASONIC ENDOSCOPE

CROSS-REFERENCE TO RELATED APPLICATION

The present application claims priority under 35 U.S.C § 119(a) to Japanese Patent Application No. 2021-100120 filed on Jun. 16, 2021, which is hereby expressly incorporated by reference, in its entirety, into the present application.

BACKGROUND OF THE INVENTION

1. Field of the Invention

The present invention relates to a treatment tool elevating mechanism and an ultrasonic endoscope.

2. Description of the Related Art

Conventionally, there is known an endoscope comprising an elevator that is provided at a distal end portion of an insertion part to be inserted into a body cavity, in which a treatment tool that is inserted into a treatment tool insertion channel and led out from a treatment tool lead-out portion of the distal end portion is elevated by an elevator and an elevation angle of the elevator is changed so that a lead-out direction of the treatment tool can be adjusted.

For example, JP2005-287593A below discloses an ultrasonic endoscope in which an elevator is provided at a treatment tool lead-out portion, an elevating lever is connected through a rotary shaft portion of the elevator, an operation wire connected to the elevating lever is pushed and pulled by operation of an operation part to change an orientation of the elevator.

SUMMARY OF THE INVENTION

The elevating lever and the elevator are connected by, for example, fitting a fitting shaft of the rotary shaft portion provided at one of the elevating lever or the elevator into a fitting hole provided at the other of the elevating lever or the elevator.

Incidentally, in recent years, as a treatment tool used has become multifunctional and the diameter thereof has increased, the load applied to the fitting shaft and the fitting hole upon moving the elevator has increased. It is conceivable to enlarge the fitting shaft in order to improve load bearing capacity, but there is a concern that the enlargement of the fitting shaft may increase the diameter of the endoscope to increase the burden on a patient.

The present invention has been made in view of such circumstances, and an object of the present invention is to provide a treatment tool elevating mechanism and an ultrasonic endoscope capable of restraining an increase in diameter of an endoscope and improving load bearing capacity.

There is provided a treatment tool elevating mechanism of a first aspect comprising: a rotary shaft portion that is supported so as to be rotatable about a rotation axis; an elevator that is connected to one end of the rotary shaft portion so as to be rotatable integrally with the rotary shaft portion; and an elevating lever that is connected to the other end of the rotary shaft portion so as to be rotatable integrally with the rotary shaft portion, in which a rotational force is applied to the elevating lever, and the rotational force is transmitted to the elevator through the rotary shaft portion, at least one fitted member of the elevating lever or the elevator has a fitting recessed portion that is open in a direction of the rotary shaft portion, the rotary shaft portion has a fitting protruding portion that is fitted into the fitting recessed portion so as to be non-rotatable relative to the fitting recessed portion, and the fitting protruding portion has a center of gravity at a position eccentric from the rotation axis in a cross-section perpendicular to the rotation axis.

In the treatment tool elevating mechanism of a second aspect, the fitted member is the elevator.

In the treatment tool elevating mechanism of a third aspect, the elevator has a treatment tool support portion extending in a direction orthogonal to the rotation axis from the rotation axis, and the fitting protruding portion has a center of gravity at a position eccentric in an extension direction of the treatment tool support portion from the rotation axis in a cross-section perpendicular to the rotation axis.

In the treatment tool elevating mechanism of a fourth aspect, the fitted member is the elevating lever.

In the treatment tool elevating mechanism of a fifth aspect, the elevating lever has a lever portion extending in a direction orthogonal to the rotation axis from the rotation axis, and the fitting protruding portion has a center of gravity at a position eccentric in an extension direction of the lever portion from the rotation axis in a cross-section perpendicular to the rotation axis.

In the treatment tool elevating mechanism of a sixth aspect, the fitted member is the elevator and the elevating lever, the fitting recessed portion has a first fitting recessed portion that is provided in the elevator and that is open in the direction of the rotary shaft portion, and a second fitting recessed portion that is provided in the elevating lever and that is open in the direction of the rotary shaft portion, the fitting protruding portion has a first fitting protruding portion that is provided at the one end of the rotary shaft portion and that is fitted into the first fitting recessed portion so as to be non-rotatable relative to the first fitting recessed portion, and a second fitting protruding portion that is provided at the other end of the rotary shaft portion and that is fitted into the second fitting recessed portion so as to be non-rotatable relative to the second fitting recessed portion, and the first fitting protruding portion and the second fitting protruding portion each have a center of gravity at a position eccentric from the rotation axis in a cross-section perpendicular to the rotation axis.

In the treatment tool elevating mechanism of a seventh aspect, the elevator has a treatment tool support portion extending in a direction orthogonal to the rotation axis from the rotation axis, the elevating lever has a lever portion extending in a direction orthogonal to the rotation axis from the rotation axis, the first fitting protruding portion has the center of gravity at a position eccentric in an extension direction of the treatment tool support portion from the rotation axis in a cross-section perpendicular to the rotation axis, and the second fitting protruding portion has the center of gravity at a position eccentric in an extension direction of the lever portion from the rotation axis in a cross-section perpendicular to the rotation axis.

In the treatment tool elevating mechanism of an eighth aspect, a sealing portion is further provided between the elevator and the elevating lever.

In the treatment tool elevating mechanism of a ninth aspect, a holding portion having a holding hole by which the rotary shaft portion is rotatably held is further provided, and the sealing portion is disposed between an outer peripheral surface of the rotary shaft portion and an inner peripheral surface of the holding hole.

In the treatment tool elevating mechanism of a tenth aspect, the fitting protruding portion is included in a formation region of the rotary shaft portion in a case where the fitting protruding portion and the rotary shaft portion are projected onto a plane orthogonal to the rotation axis.

In the treatment tool elevating mechanism of an eleventh aspect, the fitting recessed portion has a closed shape in a cross-section perpendicular to the rotation axis.

There is provided an ultrasonic endoscope of a twelfth aspect comprising: the treatment tool elevating mechanism according to any one of the above.

According to the present invention, it is possible to provide a treatment tool elevating mechanism and an ultrasonic endoscope capable of restraining an increase in diameter of an endoscope and improving load bearing capacity.

BRIEF DESCRIPTION OF THE DRAWINGS

FIG. 5 is a perspective view of the entire elevator assembly as viewed from the left side.

FIG. 6 is a perspective view of the entire elevator assembly as viewed from the right side.

FIGS. 7A and 7B are views of an elevating lever, an elevator, and a rotary shaft portion as viewed in a direction parallel to the rotation axis from the left side.

FIG. 8 is a cross-sectional view taken along line 8-8 in FIG. 3 as viewed in an arrow direction.

DESCRIPTION OF THE PREFERRED EMBODIMENTS

Hereinafter, preferred embodiments of a treatment tool elevating mechanism according to the embodiments and an ultrasonic endoscope comprising the treatment tool elevating mechanism will be described with reference to the accompanying drawings.

Figure 1:
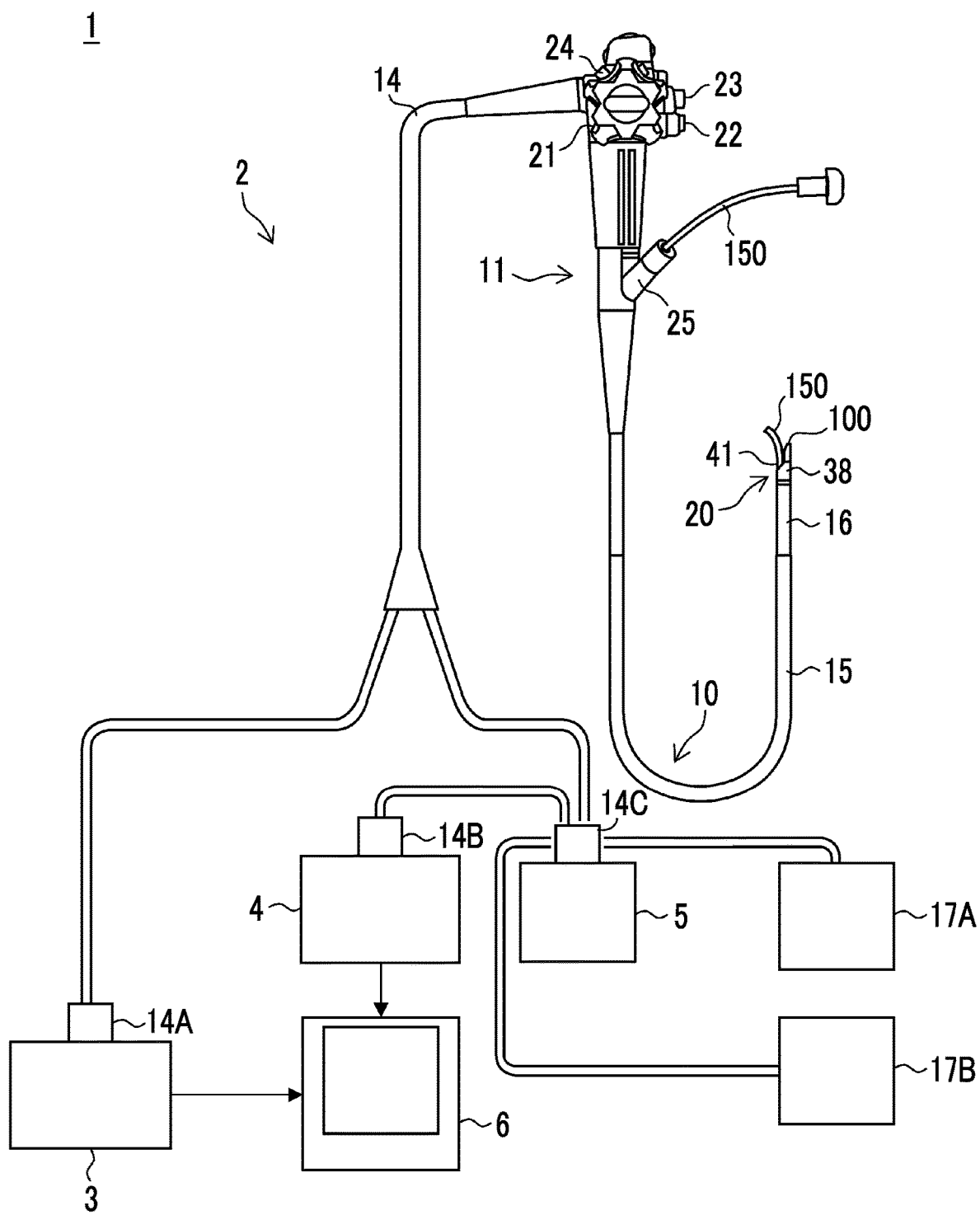
FIG. 1 is a schematic configuration view showing an example of a configuration of an ultrasonography system.

FIG. 1 is an overall configuration view of an ultrasonography system 1.

The ultrasonography system 1 comprises an ultrasonic endoscope 2 that captures an endoscopic image and an ultrasonic image in a body, an ultrasound processor unit 3 that generates the ultrasonic image, an endoscope processor unit 4 that generates the endoscopic image, a light source device 5 that supplies illumination light with which the inside of the body is illuminated to the ultrasonic endoscope 2, and a monitor 6 that displays the endoscopic image and the ultrasonic image.

The ultrasonic endoscope 2 is a convex type ultrasonic endoscope, has a distal end and a proximal end, and is formed of an insertion part 10 that is inserted into the body, an operation part 11 that is consecutively provided at the proximal end of the insertion part 10, and a universal cord 14 of which the proximal end portion is connected to the operation part 11. Connectors 14A, 14B, and 14C that are used to connect the ultrasonic endoscope 2 to the ultrasound processor unit 3, the endoscope processor unit 4, and the light source device 5, respectively, are provided at the distal end portions of the universal cord 14. In addition, the ultrasonography system 1 further comprises a water supply tank 17A that stores wash water and the like, and a suction pump 17B that sucks a suction substance (including the supplied wash water and the like) in the body cavity.

The insertion part 10 is constituted of a soft portion 15, a bendable portion 16, and a distal end portion 20 that are consecutively provided in order from the proximal end to the distal end.

The soft portion 15 is flexible and is bent in any direction along the insertion path of the insertion part 10. The bendable portion 16 is bent in each of the up-down and right-left directions by the operation of an angle knob 21 of the operation part 11.

The distal end portion 20 comprises an ultrasound observation part 100 in which ultrasonic waves are transmitted to and received from the distal end thereof, the received ultrasonic waves are converted into ultrasonic signals that are electrical signals, and the ultrasonic signals are output. The ultrasonic signals output from the ultrasound observation part 100 are sent to the ultrasound processor unit 3 connected by the universal cord 14, and the ultrasound processor unit 3 generates a tomographic image of the cell tissue existing in the depth direction of the body wall part irradiated with ultrasonic waves as the ultrasonic image.

In addition, the distal end portion 20 comprises an endoscope observation part 38 in which an observed part in the body is imaged, and the endoscope observation part 38 is provided on the proximal end side with respect to the ultrasound observation part 100. The image captured in the endoscope observation part 38 is sent to the endoscope processor unit 4 connected by the universal cord 14 as an observation image (endoscopic image), and illumination light emitted by an illumination unit is propagated from the light source device 5 connected by the universal cord 14, through a light guide provided inside the ultrasonic endoscope 2.

Further, the distal end portion 20 comprises a treatment tool lead-out portion 41 provided on the proximal end side with respect to the ultrasound observation part 100. The treatment tool lead-out portion 41 leads out a treatment tool 150 inserted into a treatment tool insertion channel provided inside the insertion part 10, from a treatment tool inlet port 25 of the operation part 11 to the outside of the insertion part 10. The treatment tool lead-out portion 41 is provided with an elevator 50, which will be described later, that adjusts the lead-out direction of the treatment tool 150.

Figure 2:
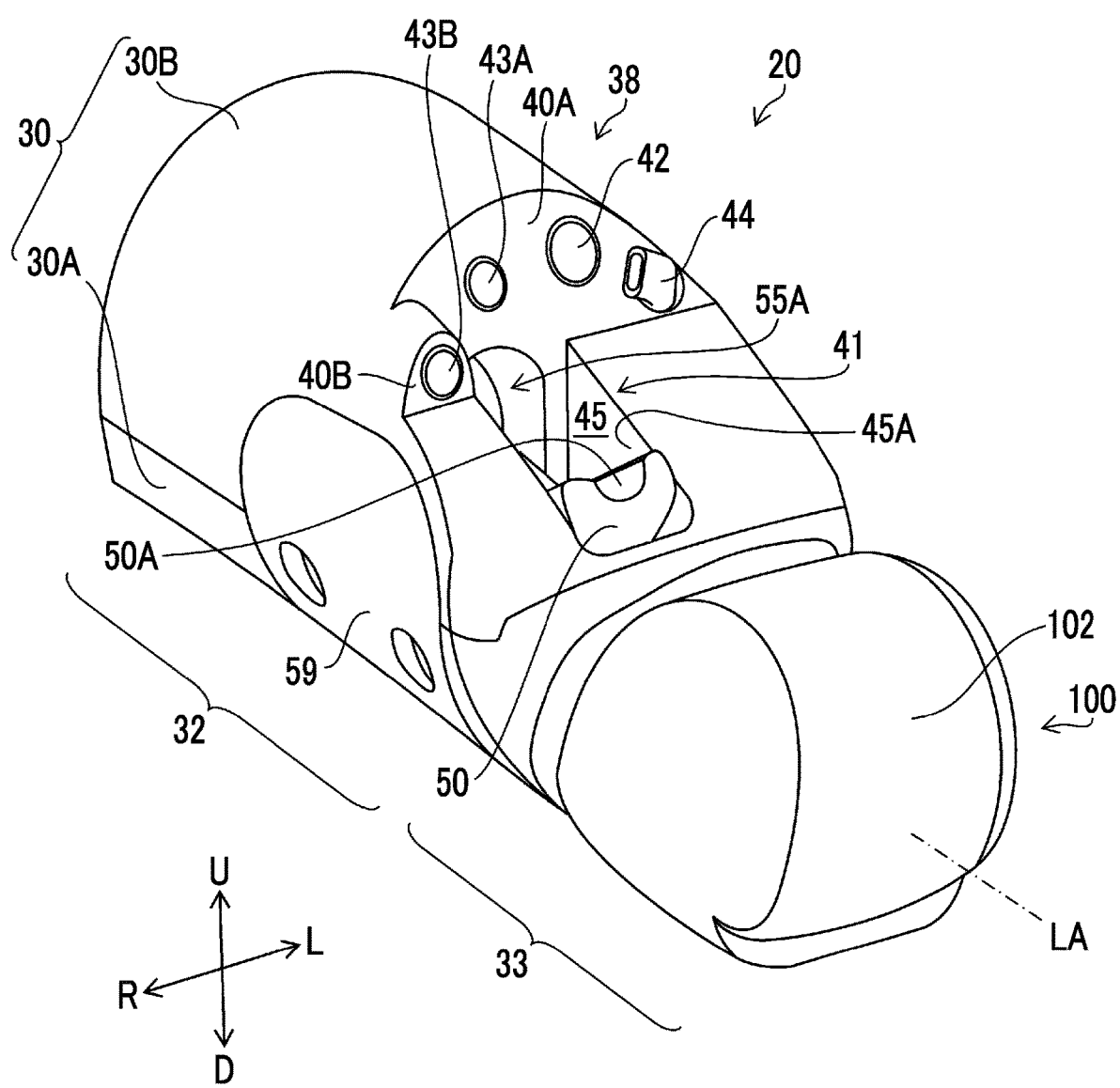
FIG. 2 is an external perspective view of a distal end portion of an insertion part.
Figure 3:
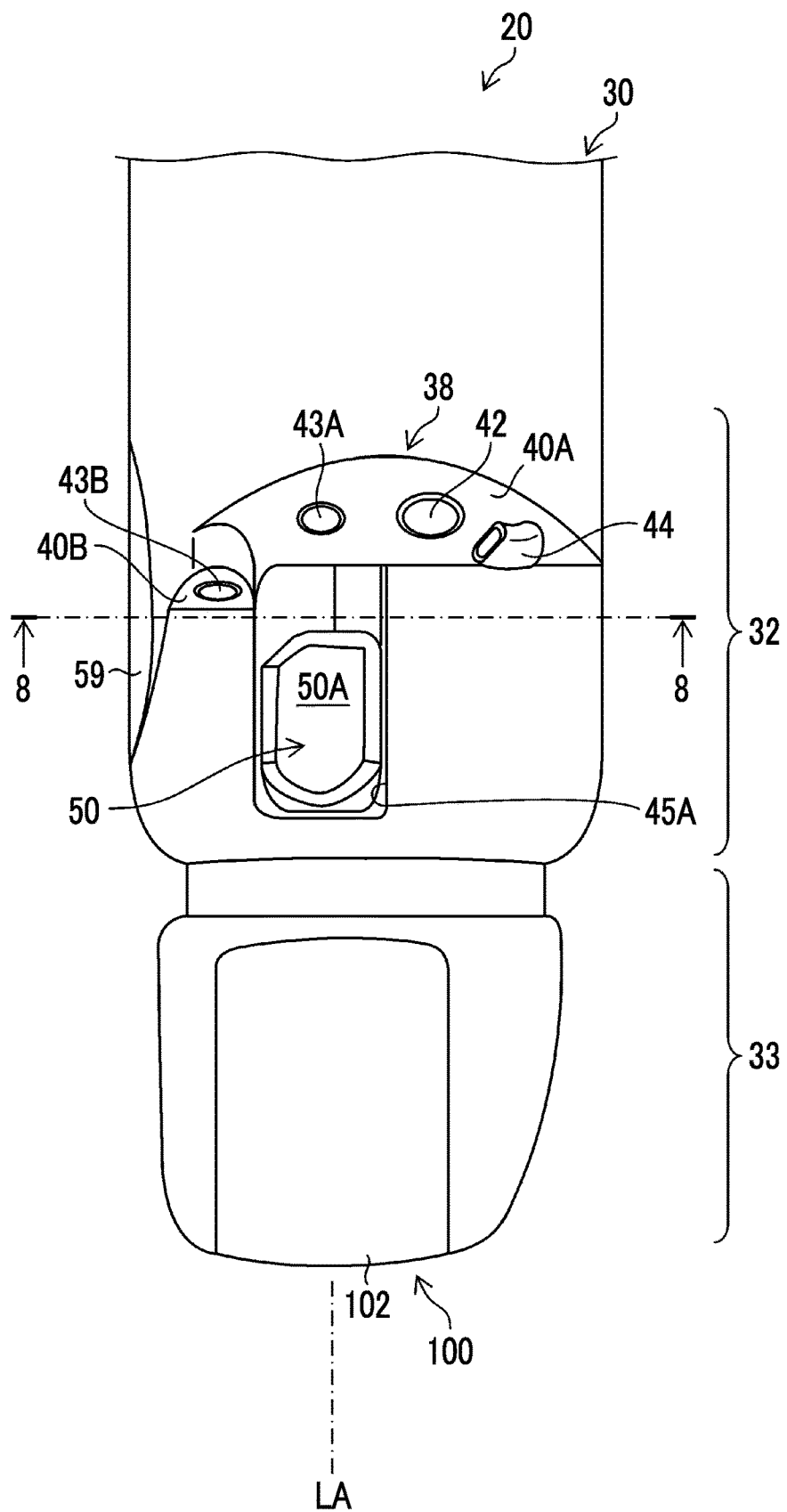
FIG. 3 is a top view of the distal end portion of the insertion part.

Next, the configuration of the distal end portion 20 will be described. FIGS. 2 and 3 are a perspective view and a plan view (top view) showing the appearance of the distal end portion 20, respectively.

The distal end portion 20 comprises an exterior case 30 (also referred to as a housing) corresponding to a distal end portion body. The exterior case 30 houses the respective units of the ultrasound observation part 100 and the endoscope observation part 38, and an elevator assembly 49, which will be described later.

In the exterior case 30, the part on the proximal end side with respect to the ultrasound observation part 100 is divided into two in the up-down direction in FIG. 2. Therefore, the exterior case 30 is constituted of the exterior case body 30A located on a lower side in FIG. 2 and an exterior case lid 30B located on an upper side in FIG. 2.

A lever housing lid 59 is provided so as to straddle the exterior case body 30A and the exterior case lid 30B at a position facing a lever housing portion 56 to be described later (see FIG. 6) on the side surfaces of the exterior case body 30A and the exterior case lid 30B on the R direction side.

Here, when viewed from the proximal end side toward the distal end side of the insertion part 10 in a direction parallel to a longitudinal axis LA of the insertion part 10, among the directions perpendicular to the longitudinal axis LA of the insertion part 10, the direction in which the ultrasound observation part 100 and the treatment tool lead-out portion 41 are disposed is set as the up and the opposite direction thereto is set as the down, and the up (U), down (D), left (L), and right (R) are used as the terms relating to the directions.

Although details are omitted, a part of the exterior case 30 can be detached as a separate block, and constituent components can be assembled into a predetermined housing portion in a state in which the separate block is detached. After the constituent components are assembled into the housing portion, the separate block is attached to the exterior case 30 (for example, the exterior case body 30A, the exterior case lid 30B, and the like), whereby the constituent components are housed and held in the housing portion and are fixed to the distal end portion 20.

In addition, the exterior case 30 is formed of, for example, a resin material such as a methacrylic resin or a plastic including polycarbonate, as an insulating material having an insulating property.

Further, the distal end portion 20 is constituted of a proximal part 32 on the proximal end side and an extension part 33 extending from the proximal part 32 to the distal end side as shown in FIGS. 2 and 3.

The proximal part 32 is provided with the endoscope observation part 38. The extension part 33 includes the above-mentioned ultrasound observation part 100 provided on the upper surface side. The ultrasound observation part 100 has a convex type ultrasonic transducer 102 in which a large number of ultrasound oscillators that transmit and receive ultrasonic waves are arranged in a convex shape.

The endoscope observation part 38 has a first slope 40A on the left side and a second slope 40B on the right side that face diagonally upward on the distal end side, and the recessed treatment tool lead-out portion 41 provided in the middle part between the first slope 40A and the second slope 40B.

The first slope 40A is provided with an observation window 42, a first illumination window 43A, and an air/water supply nozzle 44. The second slope 40B is provided with a second illumination window 43B.

The observation window 42 is used to obtain an optical image of a subject, and acquires an image of the observed part as an observation image. An image pickup system unit in which an image formation optical system and a solid state image pickup element (a charge coupled device (CCD) type or complementary metal oxide semiconductor (CMOS) type solid state image pickup element), which are constituents of an optical observation part, are integrally assembled is housed and disposed inside the proximal part 32 on the back surface side of the observation window 42. The image pickup system unit is electrically connected to the endoscope processor unit 4 connected to the universal cord 14.

The first illumination window 43A and the second illumination window 43B irradiate the observed part with illumination light. Light emitting units that are constituents of the illumination unit and emit illumination light through the first illumination window 43A and the second illumination window 43B are housed and disposed inside the proximal part 32 on the respective back surface sides of the first illumination window 43A and the second illumination window 43B. The light emitting units are optically connected to the light source device 5, which is connected to the universal cord 14, through the light guide.

The air/water supply nozzle 44 injects water or air toward the observation window 42 by the operation of the air/water supply button 22 (see FIG. 1) of the operation part 11 to wash the observation window 42 and the like.

In the treatment tool lead-out portion 41, the elevator 50 is disposed and an elevator housing space 45 having an opening portion 45A is formed on the side surface (upper side) of the exterior case 30 as a slit-shaped space where the elevator 50 is disposed, and a treatment tool insertion hole 55A is provided on the proximal end side of the treatment tool lead-out portion 41.

The treatment tool insertion hole 55A communicates with the treatment tool inlet port 25 (see FIG. 1) of the operation part 11 through the treatment tool insertion channel (pipe line) inserted into the inside of the insertion part 10. Therefore, the treatment tool inserted from the treatment tool inlet port 25 is guided to the elevator housing space 45 from the treatment tool insertion hole 55A. Then, the lead-out direction (lead-out angle) is bent by the elevator 50 of the elevator housing space 45, and the treatment tool is led out from the treatment tool lead-out portion 41 toward the side (upper side) of the insertion part 10.

Further, the treatment tool insertion channel is also connected to the suction channel, and body fluid or the like is sucked from the treatment tool insertion hole 55A by the operation of the suction button 23 (see FIG. 1) of the operation part 11.

The elevator 50 is provided so as to be rotationally movable around a rotation axis of an axial direction including a component in a direction orthogonal to the longitudinal axis LA of the insertion part 10, and has a treatment tool support portion 50A serving as a treatment tool guide surface that guides the treatment tool led out from the treatment tool insertion channel. The treatment tool support portion 50A is formed in a recessed surface shape (arc shape) that curves upward from the proximal end side toward the distal end side of the distal end portion 20 on the upper surface side of the elevator 50.

The treatment tool led out from the treatment tool insertion hole 55A to the elevator housing space 45 is bent along the treatment tool support portion 50A upward with respect to the axial direction of the distal end portion 20 (the longitudinal axis LA direction of the insertion part 10) and is led out to the outside from the opening portion 45A on the upper side of the elevator housing space 45 serving as a treatment tool outlet port.

Further, the elevator 50 rises or lies down by the operation of the elevating operation lever 24 (see FIG. 1) of the operation part 11, and the elevator 50 is operated to rise or lie down to adjust the elevation angle from the lying state so that the lead-out direction (lead-out angle) of the treatment tool led out from the treatment tool lead-out portion 41 can be adjusted.

First Embodiment

Figure 4:
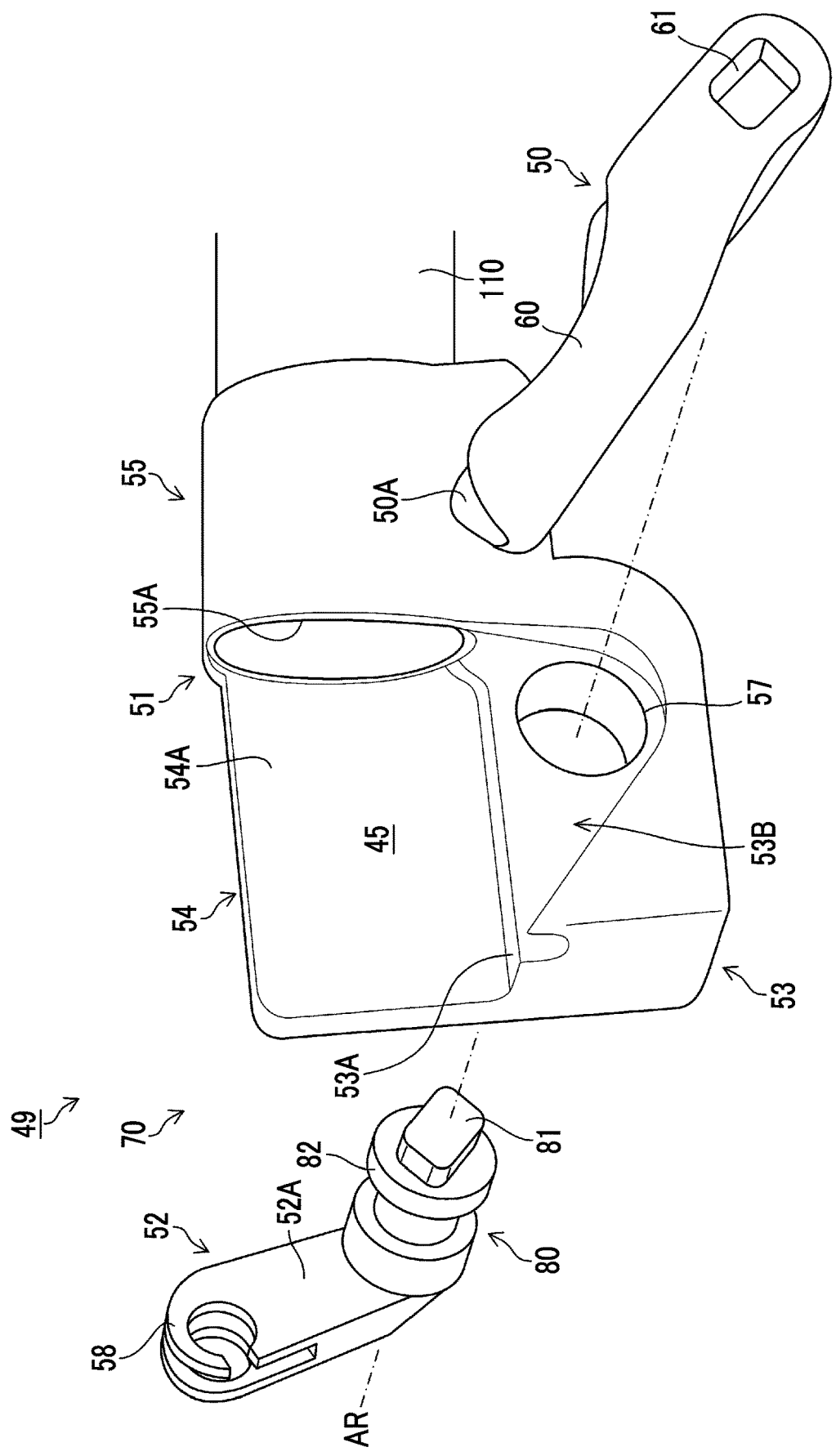
FIG. 4 is an exploded perspective view of an elevator assembly including a first embodiment of a treatment tool elevating mechanism.

Next, a first embodiment of the treatment tool elevating mechanism will be described. FIG. 4 is an exploded perspective view of the elevator assembly 49, FIG. 5 is a perspective view of the elevator assembly 49 as viewed from the left side, and FIG. 6 is a perspective view of the entire elevator assembly 49 as viewed from the right side.

The elevator assembly 49 is integrally assembled as shown in FIGS. 4 to 6, and is housed and held in a predetermined housing portion of the exterior case 30 and is fixed into the distal end portion 20.

As shown in FIG. 4, the elevator assembly 49 includes an assembly body 51 that defines the elevator housing space 45 and that supports constituent components, and a treatment tool elevating mechanism 70. The treatment tool elevating mechanism 70 comprises a rotary shaft portion 80 that is rotatably supported, the elevator 50 that is connected to one end of the rotary shaft portion 80, and an elevating lever 52 that is connected to the other end of the rotary shaft portion 80. In the treatment tool elevating mechanism 70, as will be described later, in a case where a rotational force is applied to the elevating lever 52, the rotational force is transmitted to the elevator 50 through the rotary shaft portion 80. In the first embodiment, the elevator 50 forms a fitted member having a fitting recessed portion 61.

The assembly body 51 is constituted of a base portion 53 forming the lower portion of the assembly body 51, a partition portion 54 disposed on the side of the right-side surface of the base portion 53, and a treatment tool insertion portion 55 forming the proximal end portion. The base portion 53 and the partition portion 54 form a partition wall between the elevator 50 and the elevating lever 52. These constituent portions are integrally formed, but separate constituent portions may be connected to each other to form the assembly body 51.

The base portion 53 is disposed below the elevator housing space 45 on the basis of the region of the elevator housing space 45 in a state in which the base portion 53 is housed in the distal end portion 20 (a predetermined housing portion of the exterior case 30) as the elevator assembly 49 as shown in FIGS. 2 and 3.

A recessed portion 53B is formed in a region along the left-side surface of the base portion 53. The elevator 50 can be rotatably housed in the recessed portion 53B.

The partition portion 54 extends upward at a position along the right edge portion of an upper surface 53A of the base portion 53, and the right-side wall surface of the elevator housing space 45 is formed by a left-side surface 54A of the partition portion 54.

The treatment tool insertion portion 55 is consecutively provided on the proximal end side of the base portion 53 and the partition portion 54, and the treatment tool insertion portion 55 is disposed on the proximal end side of the elevator housing space 45.

The treatment tool insertion hole 55A that is open toward the elevator housing space 45 is formed in the treatment tool insertion portion 55. A pipe line member 110 forming the treatment tool insertion channel is connected to the proximal end side of the treatment tool insertion portion 55, and the treatment tool insertion hole 55A communicates with the treatment tool insertion channel.

The lever housing portion 56 is provided in a region along the right-side surfaces of the base portion 53 and the partition portion 54 (see FIG. 6). The base portion 53 is provided with a cylindrical holding hole 57 that penetrates the lever housing portion 56 and the recessed portion 53B of the base portion 53. The base portion 53 functions as a holding portion having the holding hole 57 by which the rotary shaft portion 80 is rotatably held.

The rotary shaft portion 80 has a cylindrical shape having one end and the other end. The elevator 50 is connected to the one end of the rotary shaft portion 80 so as to be rotatable integrally with the rotary shaft portion 80, and the elevating lever 52 is connected to the other end of the rotary shaft portion 80 so as to be rotatable integrally with the rotary shaft portion 80.

The rotary shaft portion 80 comprises a fitting protruding portion 81 that is fitted into the fitting recessed portion 61 of the elevator 50, which will be described later, so as to be non-rotatable relative to the fitting recessed portion 61. The fitting protruding portion 81 protrudes in parallel with a rotation axis AR of the rotary shaft portion 80. The rotary shaft portion 80 has an outer peripheral surface provided with a housing groove 82 along the circumferential direction. A sealing portion 90 (see FIG. 8), which will be described later, is disposed in the housing groove 82.

The rotary shaft portion 80 has a circular shape in a cross-section perpendicular to the rotation axis AR. On the other hand, the fitting protruding portion 81 has a non-circular shape in a cross-section perpendicular to the rotation axis AR, and has a substantially rectangular shape in FIG. 4 as an example thereof The rotary shaft portion 80 is held by the above-mentioned holding hole 57 of the base portion 53 so as to be rotatable about the rotation axis AR. The outer diameter of the rotary shaft portion 80 (excluding the housing groove 82) and the inner diameter of the holding hole 57 substantially match each other.

The elevating lever 52 is formed in a long plate shape. The elevating lever 52 is connected to the other end of the rotary shaft portion 80 so as to be rotatable integrally with the rotary shaft portion 80. The rotary shaft portion 80 is connected to one end portion side (proximal end portion side) of the elevating lever 52 in the longitudinal direction. Further, the rotary shaft portion 80 is connected so as to be substantially orthogonal to a broad surface 52A of the elevating lever 52 facing the partition portion 54. The elevating lever 52 and the rotary shaft portion 80 may be connected to each other by integral formation, or the elevating lever 52 and the rotary shaft portion 80 as separate members may be connected by being fixed with an adhesive, a screw, or the like. The elevating lever 52 comprises a lever portion 58 extending in a direction orthogonal to the rotation axis AR from the rotation axis AR. The lever portion 58 is provided with a wire connection portion 116, which will be described later.

The elevator 50 has a bilaterally symmetrical elevator body 60 on which an arc-shaped treatment tool support portion 50A is formed, and the fitting recessed portion 61 that is formed on the side opposite to the treatment tool support portion 50A of the elevator body 60 and that is open in a direction of the rotary shaft portion 80. The fitting recessed portion 61 has a non-circular rectangular shape having the same shape as the fitting protruding portion 81 when viewed from a direction parallel to the rotation axis AR. In FIG. 4, the fitting recessed portion 61 penetrates the elevator body 60 when viewed from the direction parallel to the rotation axis AR. On the other hand, the fitting recessed portion 61 has a closed shape in a cross-section perpendicular to the rotation axis AR. Therefore, in the closed shape, the entire circumference of the fitting recessed portion 61 is surrounded by the elevator body 60, and a cutout portion, such as a C-shape or a U-shape, is not provided.

As shown in FIG. 5, the elevator assembly 49 is integrally assembled. In assembly, the rotary shaft portion 80 provided in the elevating lever 52 is inserted into the holding hole 57 from the lever housing portion 56 side (see FIG. 6) toward the recessed portion 53B. The rotary shaft portion 80 is rotatably supported by the holding hole 57. Only the fitting protruding portion 81 of the rotary shaft portion 80 protrudes from the holding hole 57 to the recessed portion 53B (see FIG. 8).

The elevator 50 is disposed from the recessed portion 53B side, and the fitting protruding portion 81 of the rotary shaft portion 80 and the fitting recessed portion 61 of the elevator 50 are fitted so as to be non-rotatable relative to each other. The fitting protruding portion 81 and the fitting recessed portion 61 are fitted to each other, whereby the elevator 50 is connected to the one end of the rotary shaft portion 80 so as to be rotatable integrally with the rotary shaft portion 80. When the rotary shaft portion 80 is inserted into the holding hole 57 and the fitting protruding portion 81 of the rotary shaft portion 80 and the fitting recessed portion 61 of the elevator 50 are fitted to each other, the rotary shaft portion 80 is positioned in the holding hole 57.

The sealing portion 90 such as an O-ring is disposed on the outer peripheral surface of the housing groove 82 (see FIG. 8) before the rotary shaft portion 80 is inserted into the holding hole 57.

As shown in FIG. 6, the lever housing portion 56 is provided in the region along the right-side surfaces of the base portion 53 and the partition portion 54, and the elevating lever 52 is housed therein so as to be rotatable integrally with the rotary shaft portion 80.

A control cable 112 is connected to the proximal end side of the lever housing portion 56 in the proximal end part of the treatment tool insertion portion 55 of the assembly body 51. The control cable 112 is constituted of a guide tube 114 and an operation wire 113 inserted into the guide tube 114.

The operation wire 113 has one end (proximal end) connected to the elevating operation lever 24 of the operation part 11, and is pushed and pulled by the operation of the elevating operation lever 24. The other end (distal end) of the operation wire 113 is inserted into the inside of the lever housing portion 56 and is connected to the lever portion 58 of the elevating lever 52 through the wire connection portion 116.

In FIG. 6, the lever housing lid 59 covering the lever housing portion 56 in which the elevating lever 52 is housed is omitted.

With the treatment tool elevating mechanism 70, in a case where the operation wire 113 is pushed and pulled by the operation of the elevating operation lever 24, a rotational force is applied to the elevating lever 52 so that the rotary shaft portion 80 is rotated about the rotation axis AR integrally with the elevating lever 52. The rotational force is transmitted to the elevator 50 through the rotary shaft portion 80. The elevator 50 is rotated integrally with the rotary shaft portion 80, and the elevator 50 rises or lies down.

The operation wire 113 is provided from the operation part 11 to the exterior case 30 by way of the insertion part 10, and is a form of a transmission member that transmits the displacement amount generated in the elevating operation lever 24 to the elevating lever 52. Other forms may be used as long as the transmission member transmits the displacement amount to the elevating lever 52.

FIGS. 7A and 7B are views of the elevating lever 52, the elevator 50, and the rotary shaft portion 80 as viewed from the left side in the direction parallel to the rotation axis AR.

FIG. 7A shows a state before the fitting recessed portion 61 and the fitting protruding portion 81 are fitted to each other. The rotary shaft portion 80 extends from the elevating lever 52 in parallel to the rotation axis AR (direction orthogonal to the paper surface). The rotary shaft portion 80 has a cylindrical shape and has a circular shape in a cross-section perpendicular to the rotation axis AR, and the rotation axis AR match the center of the circular cross-section of the rotary shaft portion 80.

The fitting protruding portion 81 has a substantially rectangular shape in a cross-section perpendicular to the rotation axis AR. The lengths of two facing sides are the same, and the lengths of two adjacent sides are different from each other. As shown in FIG. 7A, the intersection of two virtual straight lines each connecting the center of the two facing sides of the fitting protruding portion 81 is a center of gravity G of the fitting protruding portion 81. As shown in FIG. 7A, the fitting protruding portion 81 has the center of gravity G at a position eccentric from the rotation axis AR in a cross-section perpendicular to the rotation axis AR.

As shown in FIG. 7A, as described above, the elevator 50 has the elevator body 60 on which the treatment tool support portion 50A is formed and the fitting recessed portion 61 that is open in the direction of the rotary shaft portion 80.

As shown in FIG. 7B, the fitting protruding portion 81 is fitted into the fitting recessed portion 61 so as to be non-rotatable relative to the fitting recessed portion 61, whereby the treatment tool elevating mechanism 70 is assembled in which the elevating lever 52, the rotary shaft portion 80, and the elevator 50 are integrally rotatably connected to each other. As described above, the elevating operation lever 24 is operated to push and pull the operation wire 113, whereby a rotational force is applied to the elevating lever 52 in the direction indicated by the arrow and the rotary shaft portion 80 is rotated about the rotation axis AR. The rotational force is transmitted to the elevator 50 through the rotary shaft portion 80. Since the fitting protruding portion 81 and the fitting recessed portion 61 are fitted so as to be non-rotatable relative to each other, the orientation of the elevator 50 is changed (elevating and lying down) in conjunction with the rotation direction of the elevating lever 52.

In a case where the rotational force is transmitted to the elevator 50 through the rotary shaft portion 80, a load is applied to the fitting protruding portion 81 and the fitting recessed portion 61 that are fitted so as to be non-rotatable relative to each other. As the treatment tool used has become multifunctional and the diameter thereof has increased, the load applied to the fitting protruding portion 81 and the fitting recessed portion 61 has become larger.

Conventionally, there is a concern that the enlargement of the fitting protruding portion for improving the load bearing capacity may increase the diameter of the endoscope in a case where the center of gravity of the fitting protruding portion and the rotation axis match each other.

In the embodiment, the center of gravity G of the fitting protruding portion 81 is made eccentric from the rotation axis AR in a cross-section perpendicular to the rotation axis AR, so that it is possible to enlarge the fitting protruding portion 81 in the direction perpendicular to the rotation axis AR without increasing the diameter of the endoscope and to improve the load bearing capacity.

As shown in FIG. 7B, the treatment tool support portion 50A of the elevator 50 extends in the direction orthogonal to the rotation axis AR from the rotation axis AR. It is preferable that the fitting protruding portion 81 has the center of gravity G at a position eccentric in the extension direction of the treatment tool support portion 50A from the rotation axis AR in a cross-section perpendicular to the rotation axis AR. In the extension direction of the treatment tool support portion 50A, the wall thickness (in the direction perpendicular to the rotation axis AR) around the fitting recessed portion 61 into which the fitting protruding portion 81 is fitted can be secured even in a case where the center of gravity G is made eccentric, and a decrease in load bearing capacity can be restrained.

Since the fitting protruding portion 81 has a rectangular shape having two adjacent sides of which the lengths are different from each other, slipping between the fitting protruding portion 81 and the fitting recessed portion 61 can be restrained, and the rotational force of the elevating lever 52 can be reliably transmitted to the elevator 50 through the fitting protruding portion 81 of the rotary shaft portion 80 and the fitting recessed portion 61.

The rectangular shape of the fitting protruding portion 81 is shown as an example, but the shape thereof is not limited as long as the fitting protruding portion 81 can be fitted into the fitting recessed portion 61 so as to be non-rotatable relative to the fitting recessed portion 61 and the center of gravity of the fitting protruding portion 81 can be eccentric from the rotation axis AR. For example, a gear shape having protrusions and recesses on the periphery or a polygonal shape is applied.

As described above, since the fitting recessed portion 61 has a closed shape in a cross-section perpendicular to the rotation axis AR, deformation is restrained even in a case where a load is applied to the fitting recessed portion 61.

FIG. 8 is a cross-sectional view taken along line 8-8 in FIG. 3 as viewed in the arrow direction. As shown in FIG. 8, the elevating lever 52 and the rotary shaft portion 80 have a substantially L-shape in a cross-section perpendicular to the longitudinal axis LA.

The rotary shaft portion 80 is supported by the holding hole 57 so as to be rotatable about the rotation axis AR. The ring-shaped sealing portion 90 is disposed in the housing groove 82 forming the outer peripheral surface of the rotary shaft portion 80, between the elevating lever 52 and the elevator 50. Since the rotary shaft portion 80 is supported by the holding hole 57, the sealing portion 90 is disposed between the outer peripheral surface (housing groove 82) of the rotary shaft portion 80 and the inner peripheral surface of the holding hole 57.

The sealing portion 90 restrains a liquid, such as blood or water, (hereinafter, simply abbreviated as a liquid) from intruding into the lever housing portion 56 side even in a case where the liquid intrudes between the holding hole 57 and the rotary shaft portion 80 from the inside of the elevator housing space 45, so that the hard-to-wash operation wire 113 can be restrained from being contaminated.

As described above, since the fitting protruding portion 81 has the center of gravity G at a position eccentric from the rotation axis AR of the rotary shaft portion 80, it is possible to improve the load bearing capacity without increasing the diameter.

As shown in FIGS. 7A, 7B, and 8, it is preferable that the fitting protruding portion 81 is included in a formation region of the rotary shaft portion 80 in a case where the fitting protruding portion 81 and the rotary shaft portion 80 are projected onto a plane orthogonal to the rotation axis AR. Since the fitting protruding portion 81 does not affect the insertion into or removal from the holding hole 57 of the rotary shaft portion 80, assembly and repair are facilitated.

Second Embodiment

Next, a second embodiment of the treatment tool elevating mechanism will be described with reference to the drawings. The same configurations as those of the first embodiment of the treatment tool elevating mechanism are designated by the same reference numerals, and the description thereof may be omitted.

Figure 9:
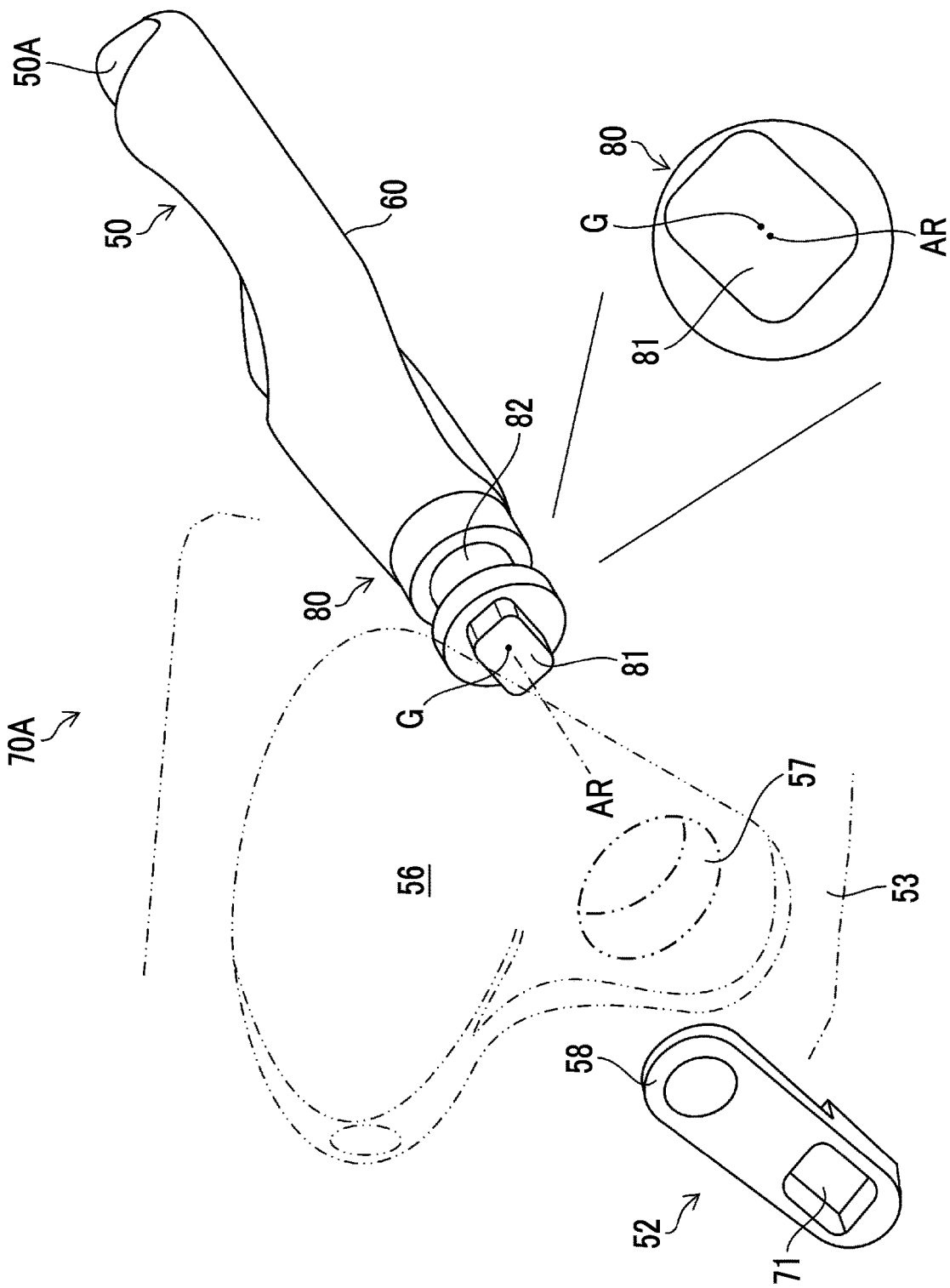
FIG. 9 is an exploded perspective view of a second embodiment of the treatment tool elevating mechanism.

FIG. 9 is an exploded perspective view of the second embodiment of the treatment tool elevating mechanism. As shown in FIG. 9, a treatment tool elevating mechanism 70A of the second embodiment comprises the rotary shaft portion 80 that is rotatably supported, the elevator 50 that is connected to one end of the rotary shaft portion 80, and the elevating lever 52 that is connected to the other end of the rotary shaft portion 80, as in the treatment tool elevating mechanism 70. The second embodiment is different from the first embodiment in that the elevating lever 52 forms a fitted member having a fitting recessed portion 71.

The rotary shaft portion 80 comprises the fitting protruding portion 81 that is fitted into the fitting recessed portion 71 of the elevating lever 52 so as to be non-rotatable relative to the fitting recessed portion 71. The fitting protruding portion 81 protrudes in parallel with a rotation axis AR of the rotary shaft portion 80. The rotary shaft portion 80 has the outer peripheral surface provided with the housing groove 82 along the circumferential direction. The above-described sealing portion 90 is disposed in the housing groove 82.

The rotary shaft portion 80 has a circular shape in a cross-section perpendicular to the rotation axis AR. On the other hand, the fitting protruding portion 81 has a non-circular shape in a cross-section perpendicular to the rotation axis AR. The rotary shaft portion 80 is held by the holding hole 57 so as to be rotatable about the rotation axis AR.

The fitting protruding portion 81 has the center of gravity G at a position eccentric from the rotation axis AR in a cross-section perpendicular to the rotation axis AR, as in the first embodiment.

The center of gravity G of the fitting protruding portion 81 is made eccentric from the rotation axis AR in a cross-section perpendicular to the rotation axis AR, so that it is possible to enlarge the fitting protruding portion 81 in the direction perpendicular to the rotation axis AR without increasing the diameter of the endoscope.

The elevating lever 52 is formed in a long plate shape, has the fitting recessed portion 71 that is provided on one end portion side (proximal end portion side) in the longitudinal direction and that is open in the direction of the rotary shaft portion 80, and is provided with the lever portion 58 extending in the direction orthogonal to the rotation axis AR from the rotation axis AR. The fitting recessed portion 71 has a non-circular rectangular shape having the same shape as the fitting protruding portion 81 when viewed from the direction parallel to the rotation axis AR. The fitting recessed portion 71 penetrates the elevating lever 52. On the other hand, the fitting recessed portion 71 has a closed shape in a cross-section perpendicular to the rotation axis AR. Therefore, in the closed shape, the entire circumference of the fitting recessed portion 71 is surrounded by the elevating lever 52, and a cutout portion, such as a C-shape or a U-shape, is not provided.

The elevator 50 is provided with the bilaterally symmetrical elevator body 60 on which the arc-shaped treatment tool support portion 50A is formed. The rotary shaft portion 80 has the one end connected to the elevator 50 on the side opposite to the treatment tool support portion 50A of the elevator body 60 so as to be rotatable integrally with the elevator 50. The elevator 50 and the rotary shaft portion 80 may be connected to each other by integral formation, or the elevator 50 and the rotary shaft portion 80 as separate members may be connected by being fixed with an adhesive, a screw, or the like. The elevator 50 and the rotary shaft portion 80 have a substantially L-shape in a cross-section perpendicular to the longitudinal axis LA (not shown).

In a case where the fitting protruding portion 81 is fitted into the fitting recessed portion 71 so as to be non-rotatable relative to the fitting recessed portion 71, the elevating lever 52 is connected to the other end of the rotary shaft portion 80 so as to be rotatable integrally with the rotary shaft portion 80, whereby the treatment tool elevating mechanism 70A is assembled in which the elevating lever 52, the rotary shaft portion 80, and the elevator 50 are integrally rotatably connected to each other.

In the second embodiment, it is preferable that the fitting protruding portion 81 has the center of gravity at a position eccentric in the extension direction of the lever portion 58 from the rotation axis AR in a cross-section perpendicular to the rotation axis AR. In the extension direction of the lever portion 58, the wall thickness (in the direction perpendicular to the rotation axis AR) around the fitting recessed portion 71 into which the fitting protruding portion 81 is fitted can be secured even in a case where the center of gravity G is made eccentric, and a decrease in load bearing capacity can be restrained.

Third Embodiment

Next, a third embodiment of the treatment tool elevating mechanism will be described with reference to the drawings. The same configurations as those of the first and second embodiments of the treatment tool elevating mechanism are designated by the same reference numerals, and the description thereof may be omitted.

Figure 10:
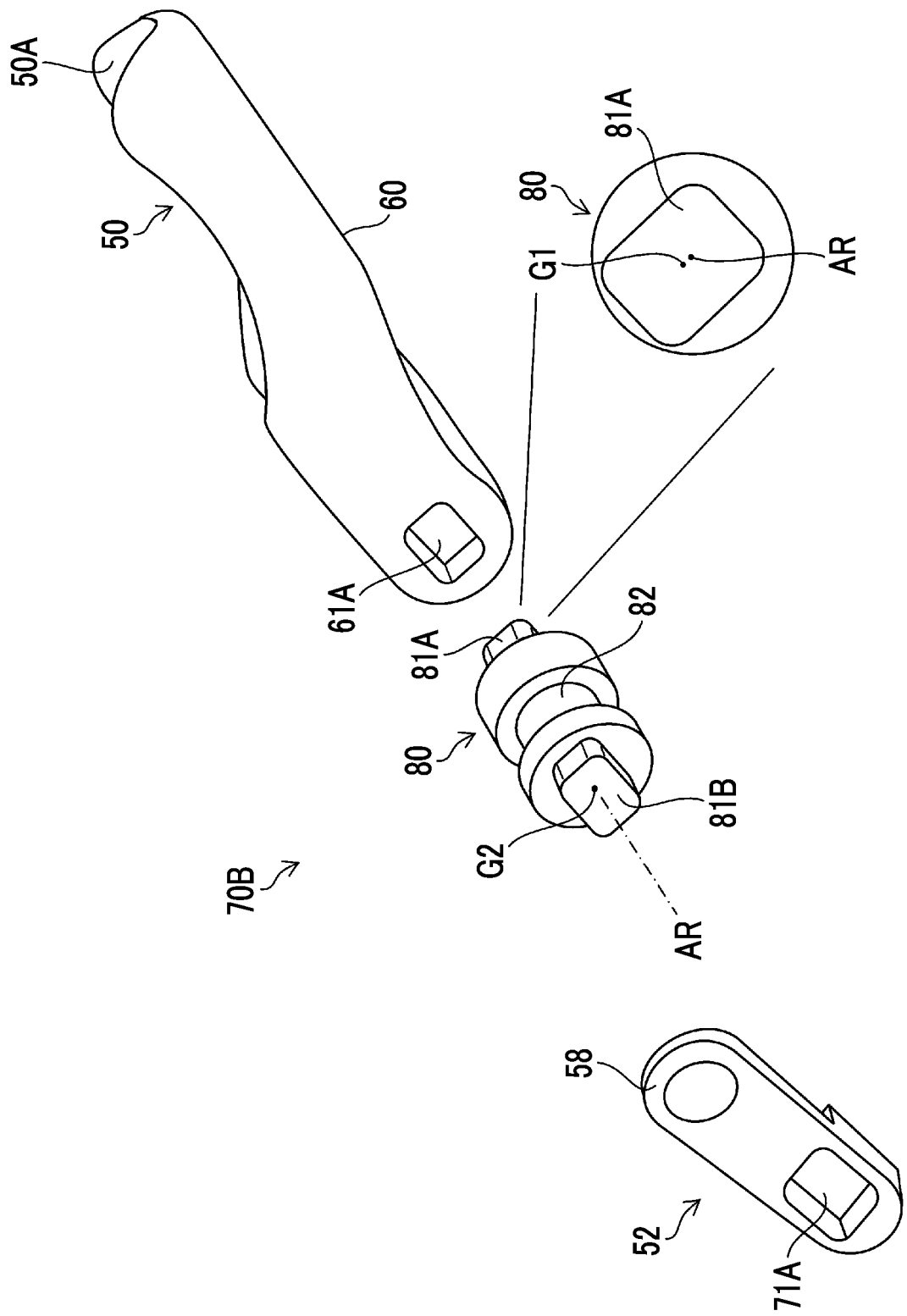
FIG. 10 is an exploded perspective view of a third embodiment of the treatment tool elevating mechanism.

FIG. 10 is an exploded perspective view of the third embodiment of the treatment tool elevating mechanism. As shown in FIG. 10, a treatment tool elevating mechanism 70B of the third embodiment comprises the rotary shaft portion 80 that is rotatably supported, the elevator 50 that is connected to one end of the rotary shaft portion 80, and the elevating lever 52 that is connected to the other end of the rotary shaft portion 80, as in the treatment tool elevating mechanisms 70 and 70A. The third embodiment is different from the first and second embodiments in that the elevator 50 has a first fitting recessed portion 61A that is open in the direction of the rotary shaft portion 80 and the elevating lever 52 has a second fitting recessed portion 71A that is open in the direction of the rotary shaft portion 80, as the fitting recessed portions. Further, a first fitting protruding portion 81A that is provided at the one end of the rotary shaft portion 80 and is fitted into the first fitting recessed portion 61A so as to be non-rotatable relative to the first fitting recessed portion 61A, and a second fitting protruding portion 81B that is provided at the other end of the rotary shaft portion 80 and is fitted into the second fitting recessed portion 71A so as to be non-rotatable relative to the second fitting recessed portion 71A are provided as the fitting protruding portions. The rotary shaft portion 80 is held by the holding hole 57 (not shown) so as to be rotatable about the rotation axis AR.

The rotary shaft portion 80 comprises the first fitting protruding portion 81A provided at the one end and the second fitting protruding portion 81B provided at the other end. The first fitting protruding portion 81A and the second fitting protruding portion 81B protrude in parallel with the rotation axis AR of the rotary shaft portion 80. The rotary shaft portion 80 has the outer peripheral surface provided with the housing groove 82 along the circumferential direction. The above-described sealing portion 90 is disposed in the housing groove 82.

The rotary shaft portion 80 has a circular shape in a cross-section perpendicular to the rotation axis AR. On the other hand, the first fitting protruding portion 81A and the second fitting protruding portion 81B each have a non-circular shape in a cross-section perpendicular to the rotation axis AR.

The elevating lever 52 is formed in a long plate shape, has the second fitting recessed portion 71A that is provided on one end portion side (proximal end portion side) in the longitudinal direction and that is open in the direction of the rotary shaft portion 80, and is provided with the lever portion 58 extending in the direction orthogonal to the rotation axis AR from the rotation axis AR. The second fitting recessed portion 71A penetrates the elevating lever 52. On the other hand, the second fitting recessed portion 71A has a closed shape in a cross-section perpendicular to the rotation axis AR.

The elevator 50 is provided with the bilaterally symmetrical elevator body 60 on which the arc-shaped treatment tool support portion 50A is formed. The first fitting recessed portion 61A that is open in the direction of the rotary shaft portion 80 is provided on the side opposite to the treatment tool support portion 50A of the elevator body 60. The first fitting recessed portion 61A penetrates the elevator 50. On the other hand, the first fitting recessed portion 61A has a closed shape in a cross-section perpendicular to the rotation axis AR.

In a case where the first fitting protruding portion 81A is fitted into the first fitting recessed portion 61A so as to be non-rotatable relative to the first fitting recessed portion 61A and the second fitting protruding portion 81B is fitted into the second fitting recessed portion 71A so as to be non-rotatable relative to the second fitting recessed portion 71A, the elevator 50 is connected to the one end of the rotary shaft portion 80 so as to be rotatable integrally with the rotary shaft portion 80, and the elevating lever 52 is connected to the other end of the rotary shaft portion 80 so as to be rotatable integrally with the rotary shaft portion 80, whereby the treatment tool elevating mechanism 70B is assembled in which the elevating lever 52, the rotary shaft portion 80, and the elevator 50 are integrally rotatably connected to each other.

The enlarged view is a view of the first fitting protruding portion 81A as viewed in a direction parallel to the rotation axis AR from the elevator 50 side. In the third embodiment, the first fitting protruding portion 81A and the second fitting protruding portion 81B have the centers of gravity G1 and G2 at positions eccentric from the rotation axis AR in a cross-section perpendicular to the rotation axis AR, respectively.

The center of gravity G1 of the first fitting protruding portion 81A is made eccentric from the rotation axis AR in a cross-section perpendicular to the rotation axis AR, so that it is possible to enlarge the first fitting protruding portion 81A in the direction perpendicular to the rotation axis AR without increasing the diameter of the endoscope.

The center of gravity G2 of the second fitting protruding portion 81B is made eccentric from the rotation axis AR in a cross-section perpendicular to the rotation axis AR, so that it is possible to enlarge the second fitting protruding portion 81B in the direction perpendicular to the rotation axis AR without increasing the diameter of the endoscope. The center of gravity G1 is preferably eccentric in the extension direction of the treatment tool support portion 50A from the rotation axis AR, and the center of gravity G2 is preferably eccentric in the extension direction of lever portion 58 from the rotation axis AR, as in the first and second embodiments.

Although the present invention has been described above, the present invention is not limited to the above examples, and various improvements or modifications may be made without departing from the gist of the present invention.

EXPLANATION OF REFERENCES

1: ultrasonography system
2: ultrasonic endoscope
3: ultrasound processor unit
4: endoscope processor unit
5: light source device
6: monitor
10: insertion part
11: operation part
14: universal cord
14A: connector
14B: connector
14C: connector
15: soft portion
16: bendable portion
17A: water supply tank
17B: suction pump
20: distal end portion
21: angle knob
22: air/water supply button
23: suction button
24: elevating operation lever
25: treatment tool inlet port
30: exterior case
30A: exterior case body
30B: exterior case lid
32: proximal part
33: extension part
38: endoscope observation part
40A: first slope
40B: second slope
41: treatment tool lead-out portion
42: observation window
43A: first illumination window
43B: second illumination window
44: air/water supply nozzle
45: elevator housing space
45A: opening portion
49: elevator assembly
50: elevator
50A: treatment tool support portion
51: assembly body
52: elevating lever
52A: broad surface
53: base portion
53A: upper surface
53B: recessed portion
54: partition portion
54A: left-side surface
55: treatment tool insertion portion
55A: treatment tool insertion hole
56: lever housing portion
57: holding hole
58: lever portion
59: lever housing lid
60: elevator body
61: fitting recessed portion
61A: first fitting recessed portion
70: treatment tool elevating mechanism
70A: treatment tool elevating mechanism
70B: treatment tool elevating mechanism
71: fitting recessed portion
71A: second fitting recessed portion
80: rotary shaft portion
81: fitting protruding portion
81A: first fitting protruding portion
81B: second fitting protruding portion
82: housing groove
90: sealing portion
100: ultrasound observation part
102: ultrasonic transducer
110: pipe line member
112: control cable
113: operation wire
114: guide tube
116: wire connection portion
150: treatment tool
R: rotation axis
G, G1, G2 center of gravity
LA: longitudinal axis

What is claimed is:

1. A treatment tool elevating mechanism comprising:
a rotary shaft portion that is supported so as to be rotatable about a rotation axis;
an elevator that is connected to one end of the rotary shaft portion so as to be rotatable integrally with the rotary shaft portion; and
an elevating lever that is connected to the other end of the rotary shaft portion so as to be rotatable integrally with the rotary shaft portion,
wherein a rotational force is applied to the elevating lever, and the rotational force is transmitted to the elevator through the rotary shaft portion,
at least one fitted member of the elevating lever or the elevator has a fitting recessed portion that is open in a direction of the rotary shaft portion,
the rotary shaft portion has a fitting protruding portion that is fitted into the fitting recessed portion so as to be non-rotatable relative to the fitting recessed portion, and
the fitting protruding portion has a center of gravity at a position eccentric from the rotation axis in a cross-section perpendicular to the rotation axis.

2. The treatment tool elevating mechanism according to claim 1,
wherein the fitted member is the elevator.

3. The treatment tool elevating mechanism according to claim 2,
wherein the elevator has a treatment tool support portion extending in a direction orthogonal to the rotation axis from the rotation axis, and
the fitting protruding portion has a center of gravity at a position eccentric in an extension direction of the treatment tool support portion from the rotation axis in a cross-section perpendicular to the rotation axis.

4. The treatment tool elevating mechanism according to claim 1,
wherein the fitted member is the elevating lever.

5. The treatment tool elevating mechanism according to claim 4,
wherein the elevating lever has a lever portion extending in a direction orthogonal to the rotation axis from the rotation axis, and
the fitting protruding portion has a center of gravity at a position eccentric in an extension direction of the lever portion from the rotation axis in a cross-section perpendicular to the rotation axis.

6. The treatment tool elevating mechanism according to claim 1,
- wherein the fitted member is the elevator and the elevating lever,
- the fitting recessed portion has a first fitting recessed portion that is provided in the elevator and that is open in the direction of the rotary shaft portion, and a second fitting recessed portion that is provided in the elevating lever and that is open in the direction of the rotary shaft portion,
- the fitting protruding portion has a first fitting protruding portion that is provided at the one end of the rotary shaft portion and that is fitted into the first fitting recessed portion so as to be non-rotatable relative to the first fitting recessed portion, and a second fitting protruding portion that is provided at the other end of the rotary shaft portion and that is fitted into the second fitting recessed portion so as to be non-rotatable relative to the second fitting recessed portion, and
- the first fitting protruding portion and the second fitting protruding portion each have a center of gravity at a position eccentric from the rotation axis in a cross-section perpendicular to the rotation axis.

7. The treatment tool elevating mechanism according to claim 6,
- wherein the elevator has a treatment tool support portion extending in a direction orthogonal to the rotation axis from the rotation axis,
- the elevating lever has a lever portion extending in a direction orthogonal to the rotation axis from the rotation axis,
- the first fitting protruding portion has the center of gravity at a position eccentric in an extension direction of the treatment tool support portion from the rotation axis in a cross-section perpendicular to the rotation axis, and
- the second fitting protruding portion has the center of gravity at a position eccentric in an extension direction of the lever portion from the rotation axis in a cross-section perpendicular to the rotation axis.

8. The treatment tool elevating mechanism according to claim 1, further comprising:
- a sealing portion provided between the elevator and the elevating lever.

9. The treatment tool elevating mechanism according to claim 8, further comprising:
- a holding portion having a holding hole by which the rotary shaft portion is rotatably held,
- wherein the sealing portion is disposed between an outer peripheral surface of the rotary shaft portion and an inner peripheral surface of the holding hole.

10. The treatment tool elevating mechanism according to claim 1,
- wherein the fitting protruding portion is included in a formation region of the rotary shaft portion in a case where the fitting protruding portion and the rotary shaft portion are projected onto a plane orthogonal to the rotation axis.

11. The treatment tool elevating mechanism according to claim 1,
- wherein the fitting recessed portion has a closed shape in a cross-section perpendicular to the rotation axis.

12. An ultrasonic endoscope comprising:
- the treatment tool elevating mechanism according to claim 1.

* * * * *